US011020037B2

(12) United States Patent
Pan et al.

(10) Patent No.: US 11,020,037 B2
(45) Date of Patent: Jun. 1, 2021

(54) R WAVE DETECTION METHOD USING PERIODICITY OF ELECTROCARDIOGRAM SIGNAL

(71) Applicant: INDUSTRY-ACADEMIC COOPERATION FOUNDATION CHOSUN UNIVERSITY, Gwangju (KR)

(72) Inventors: Sung-Bum Pan, Gwangju (KR); Gyu-Ho Choi, Gwangju (KR)

(73) Assignee: INDUSTRY-ACADEMIC COOPERATION FOUNDATION CHOSUN UNIVERSITY, Gwangju (KR)

(*) Notice: Subject to any disclaimer, the term of this patent is extended or adjusted under 35 U.S.C. 154(b) by 140 days.

(21) Appl. No.: 16/389,498

(22) Filed: Apr. 19, 2019

(65) Prior Publication Data

US 2020/0229728 A1 Jul. 23, 2020

(30) Foreign Application Priority Data

Jan. 22, 2019 (KR) .................. 10-2019-0008196

(51) Int. Cl.
*A61B 5/352* (2021.01)
*A61B 5/00* (2006.01)

(52) U.S. Cl.
CPC ............ *A61B 5/352* (2021.01); *A61B 5/7221* (2013.01)

(58) Field of Classification Search
None
See application file for complete search history.

(56) References Cited

U.S. PATENT DOCUMENTS 10,485,489 B1\* 11/2019 Belle ...................... A61B 5/726
2016/0367157 A1\* 12/2016 Blake ................... A61B 5/0428

FOREIGN PATENT DOCUMENTS

KR 10-2015-0012462 A 2/2015

OTHER PUBLICATIONS

Office action dated May 18, 2020 from Korean Patent Office in a counterpart Korean Patent Application No. 10-2019-0008196 (all the cited references are listed in this IDS.) (English translation is also submitted herewith.).

\* cited by examiner

*Primary Examiner* — Paula J Stice
(74) *Attorney, Agent, or Firm* — The PL Law Group, PLLC

(57) ABSTRACT

An R wave peak detection method uses the periodicity of an electrocardiogram signal, in which expected R wave peaks are detected from an electrocardiogram signal, and a time difference between the expected R wave peaks that are detected is calculated in order to output, as actual R wave peaks, only expected R wave peaks that are greater than a threshold time difference, thereby avoiding a case in which the R wave peaks are erroneously detected from an non-ideal electrocardiogram signal.

7 Claims, 8 Drawing Sheets

R WAVE DETECTION METHOD USING PERIODICITY OF ELECTROCARDIOGRAM SIGNAL

CROSS REFERENCE TO RELATED APPLICATION

The present application claims priority to Korean Patent Application No. 10-2019-0008196, filed Jan. 22, 2019, the entire contents of which are incorporated herein for all purposes by this reference.

BACKGROUND OF THE INVENTION

1. Field of the Invention

The present invention relates to an R wave peak detection method using the periodicity of an electrocardiogram signal and, more specifically, to an R wave peak detection method using the periodicity of an electrocardiogram signal, in which expected R wave peaks are detected from an electrocardiogram signal, and a time difference between the expected R wave peaks that are detected is calculated in order to output, as actual R wave peaks, only expected R wave peaks that are greater than a threshold time difference, thereby avoiding a case in which the R wave peaks are erroneously detected from an non-ideal electrocardiogram signal.

2. Description of the Related Art

An electrocardiogram (ECG) signal refers to a recording of the waveforms that analyzes the activity of contraction/relaxation in response to currents of the heart's muscle cells. In detail, the electrocardiogram signal records an electrical signal measured in the process of depolarization and repolarization of the cardiac atrium and ventricle and is divided into P waveform, QRS complex waveform, and T waveform, and the normal electrocardiogram signal has a periodicity repeated in the order of P waveform, QRS complex waveform, and T waveform.

FIG. 1 shows a waveform of an ideal electrocardiogram signal. Referring to FIG. 1, the fundamental waveform of an electrocardiogram signal is configured such that a P waveform is a waveform that represents the depolarization of the atria and is located in front of a QRS complex waveform, and indicates an upward wave; the QRS complex waveform is a waveform that represents the depolarization of the ventricles, in which a Q waveform is a downward deflection, an R waveform is the peak of the ventricular contraction, and an S waveform is a downward deflection; and a T waveform is a waveform that represents the repolarization of the ventricles and represents an upward wave.

Meanwhile, in order to authenticate, identify, or analyze such electrocardiogram signals through a computer, the inputted electrocardiogram signal is divided into cycles, and further, one cycle is classified into sections of waveforms. For this purpose, an R waveform peak (R-Peak), which has a sharp spike shape among the QRS complex, is detected first.

This is because R wave peak (R-Peak), which is a peak of the signal amplitude of the R waveform, is relatively higher than peaks of other waveforms and has a well-defined character so that it is easy to detect, and a period between each waveform is proceeded at a predetermined distance, whereby the interval definition and period of each waveform can be classified on the basis of the R wave peak (R-Peak).

Accordingly, much research for detecting the R wave peaks (R-Peak) is being performed, and a Pan-Tompkins algorithm is typically used. According to the Pan-Tompkins algorithm, electrocardiogram signals with normal waveforms show an R wave peak (R-Peak) having detection rate of high accuracy, but electrocardiogram signals with many non-ideal waveforms show an R wave peak R-Peak having detection rate of significantly lower accuracy.

In particular, although it is normal that a T wave peak (T-Peak), which is a signal amplitude peak of T waveform (T), appears as ½ to ¼ of R wave peak (R-Peak), there is a case that the T wave peak (T-Peak) appears non-ideally large and shows a value that is similar to or larger than the R wave peak (R-Peak), as one of non-ideal waveforms. Thus, since the T waveform (T) similar to the R waveform (R) is output as the electrocardiogram signal, there is a problem that the T wave peak (T-Peak) is erroneously detected as R wave peak R-Peak when the R wave peak R-peak is detected using the Pan-Tompkins algorithm.

Therefore, there is a need for research to prevent the problem that the accuracy of R wave peak detection is lowered due to the occurrence of such non-ideal waveforms.

SUMMARY

Accordingly, the present invention has been made keeping in mind the above problems occurring in the related art, and an object of the present invention is to provide to an R wave detection method using the periodicity of an electrocardiogram signal, which is capable of accurately detecting an actual R wave peak, even when a T waveform having characteristics similar to those of an R waveform is present in an electrocardiogram signal.

In order to achieve the above object, the present invention provides an R wave peak detection method using a periodicity of an electrocardiogram signal, including receiving the electrocardiogram signal; detecting expected R wave peaks of the electrocardiogram signal; and detecting and removing the expected R wave peaks in which a time difference between the expected R wave peaks is equal to or less than a threshold time difference and extracting remaining expected R wave peaks as actual R wave peaks.

As a preferable embodiment, the method may further include, after receiving the electrocardiogram signal, calculating a gradient by sampling amplitude values corresponding to an initial region of the electrocardiogram signal for each section based on time and removing signals preceding a section having a lowest gradient from the electrocardiogram signal.

As a preferable embodiment, the removing of signals preceding the section having the lowest gradient from the electrocardiogram signal may include setting the initial region to sample the amplitude values in the electrocardiogram signal; setting sections by dividing the set initial region by a predetermined time; sampling the amplitude values corresponding to each of the divided sections and calculating the gradient that is a variation of the amplitude values with time; and extracting the section having the lowest gradient and removing signals preceding the extracted section from the electrocardiogram signal, wherein when the expected R wave peaks are detected in the electrocardiogram signal, an initial expected R wave peak is defined as the actual R wave.

As a preferable embodiment, the expected R wave peaks of the electrocardiogram signal may be detected using a Pan-Tompkins algorithm.

As a preferable embodiment, the detecting and removing of the expected R wave peaks that are equal to or less than the threshold time difference may be performed by Equation 1 below.

$$\text{if } |R_n - R_{n+1}| \le Th \begin{cases} 0, & R_{n+1} \\ 1, & \text{None} \end{cases} \quad \text{[Equation 1]}$$

$$n = 1, 2, 3, 4, \ldots$$

wherein, $R_n$ is a time at which the nth expected R wave peak is detected, Th is a threshold time difference, and when a time difference between $R_n$ and $R_{n+1}$ is equal to or less than the threshold time difference, the expected R wave peak corresponding to $R_{n+1}$ is removed.

As a preferable embodiment, the threshold time difference may be 0.4 seconds.

In addition, the present invention further provides a computer program stored on a recording medium for performing the R wave peak detection method using the periodicity of the electrocardiogram signal in combination with a computer.

The present invention has the following excellent effects.

According to the R wave peak detection method using the periodicity of the electrocardiogram signal of the present invention, it is possible to detect an actual R wave peak through a simple equation without complex algorithm, by removing the expected R wave peak in which a time difference between initially detected R wave peaks is equal to or less than a threshold time difference, whereby the amount of calculation can be minimized, and the accuracy of R wave peak detection can be improved.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION

Figure 1:
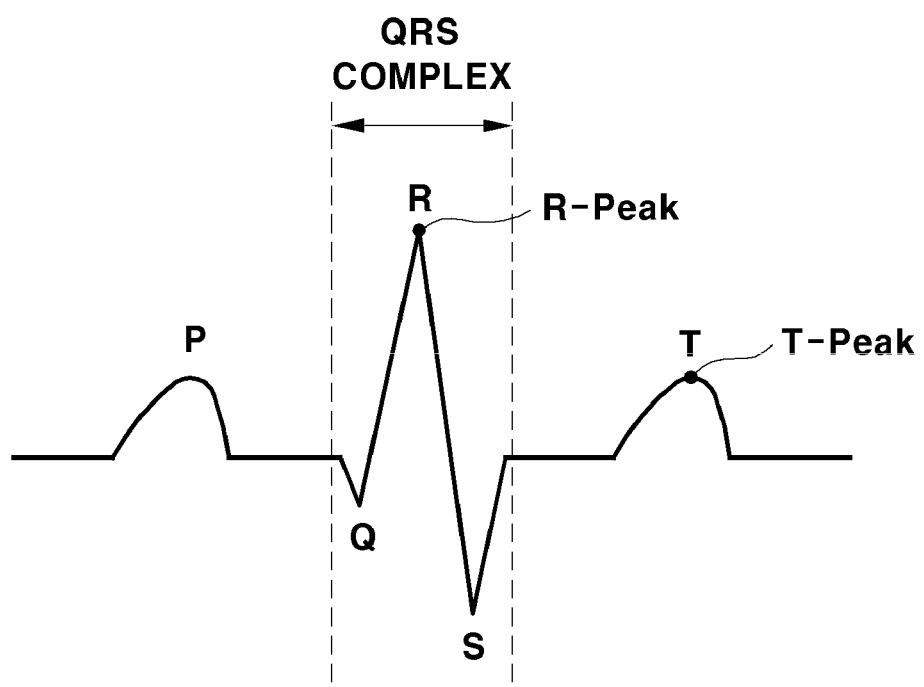
FIG. 1 is a diagram illustrating a waveform of an ideal electrocardiogram signal.

Although the terms used in the present invention have been selected as general terms that are widely used at present, there are some terms selected arbitrarily by the applicant in a specific case, and herein the meaning thereof should be grasped considering the meaning described or used in the detailed description part of the invention.

Hereinafter, the technical structure of the present invention will be described in detail with reference to preferred embodiments shown in the accompanying drawings.

However, the present invention is not limited to the embodiments described herein but may be embodied in other forms. Like reference numerals designate like elements throughout the specification.

The R wave peak detection method using the periodicity of the electrocardiogram signal according to the present invention is provided to extract expected R wave peaks, calculate a time difference between the expected R wave peaks, and remove the expected R wave peaks included in a threshold time difference, in order to prevent a T wave peak, which non-ideally appears in the input electrocardiogram signal, from being erroneously detected as the R wave peak, whereby erroneous detection of an R wave peak may be prevented by using characteristics of periodic waveforms.

Also, the R wave peak detection method using the periodicity of the electrocardiogram signal is substantially performed by a computer, and a computer program for performing the method is stored in the computer.

In addition, the computer means a general computing device including a smart device such as a smart phone or a tablet PC, as well as a general personal computer.

In addition, the computer program may be stored in a separate recording medium, and the recording medium may be designed and configured specifically for the present invention or may be known and used by those having ordinary skill in the field of computer software.

For example, the recording medium may be a magnetic medium such as a hard disk, a floppy disk and a magnetic tape, an optical recording medium such as a CD and a DVD, a magnetic-optical recording medium capable of both magnetic recording and optical recording, and a hardware device specially configured to store and execute program instructions by ROM, RAM, flash memory, and the like, or a combination thereof.

In addition, the computer program may be a program consisting of program instructions, local data files, local data structures, etc., alone or in combination, and may be program organized in high-level languages capable of being executed by a computer using an interpreter or the like as well as machine code such as that produced by the complier.

Hereinafter, an R wave peak detection method using the periodicity of an electrocardiogram signal according to an embodiment of the present invention will be described in detail.

Figure 2:
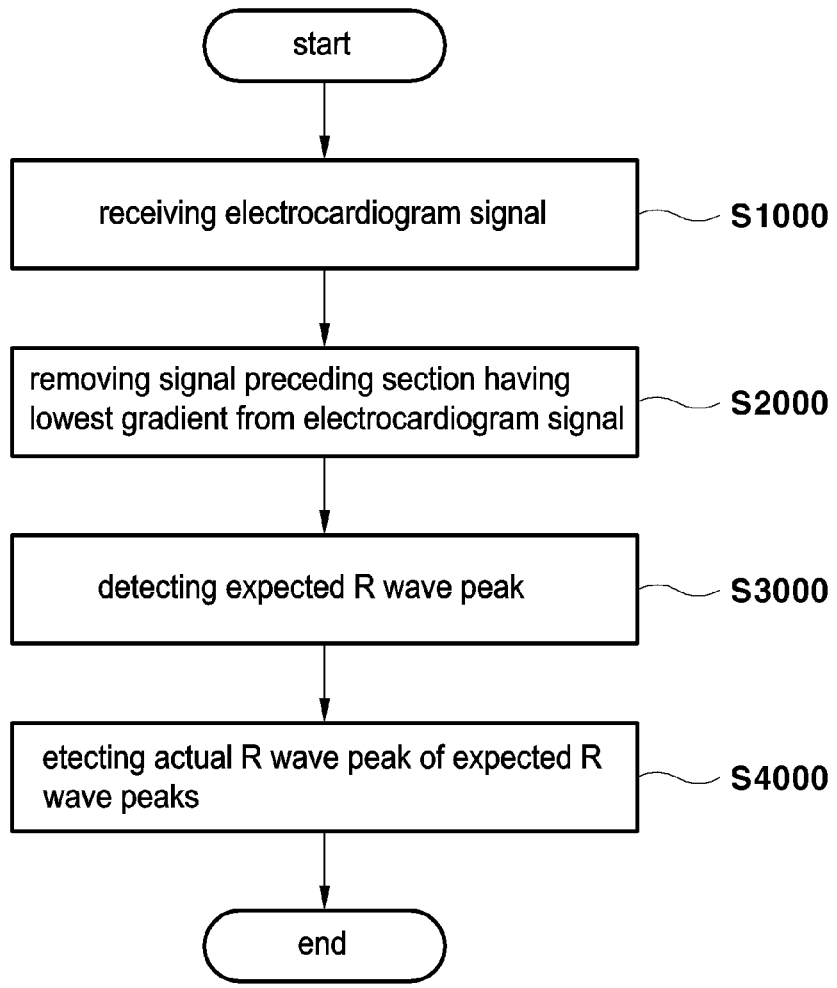
FIG. 2 is an overall flowchart illustrating an R wave peak detection method according to an embodiment of the present invention.

FIG. 2 is an overall flowchart of an R wave peak detection method according to an embodiment of the present invention. Referring to FIG. 2, an R wave peak detection method according to the present invention first receives an electrocardiogram signal (S1000).

Also, the electrocardiogram signal is measured by a standard 12-lead method based on the activity current generated according to the heartbeat, and the measured electrocardiogram signal is filtered to remove noise.

Next, a signal preceding a section having the lowest gradient is removed from the electrocardiogram signal (S2000).

Figure 3:
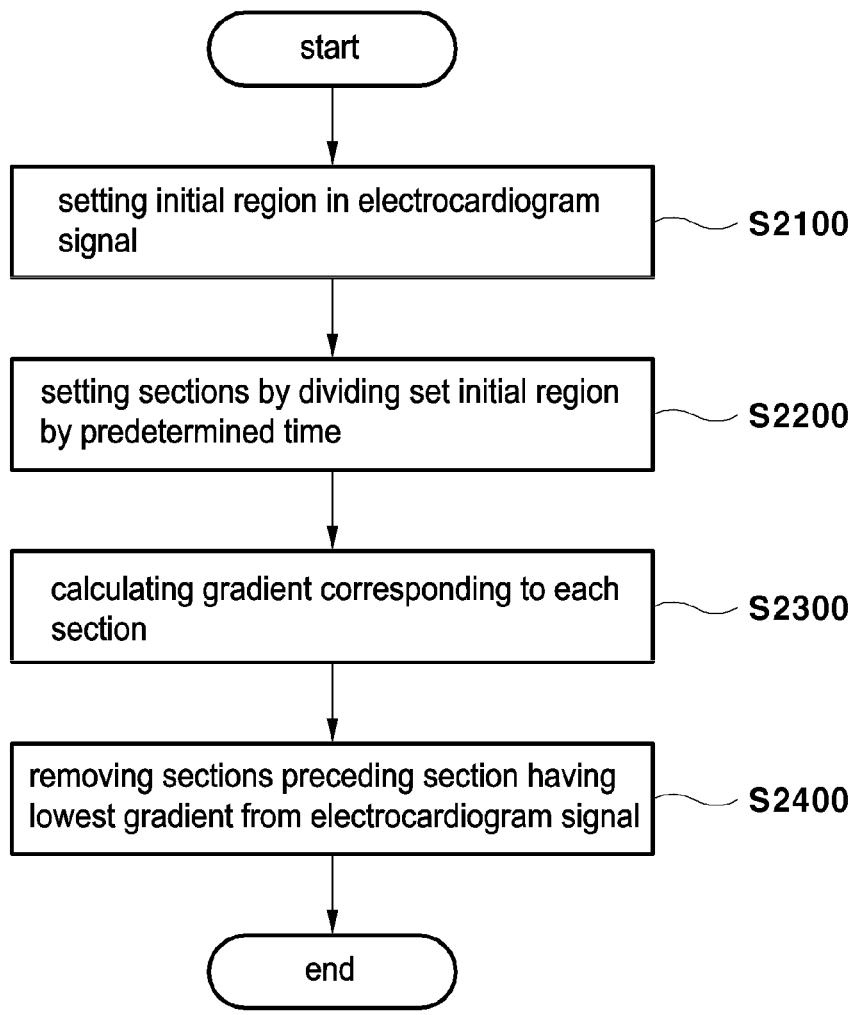
FIG. 3 is a flowchart illustrating a method of removing a signal preceding a section having the lowest gradient from an electrocardiogram signal in an R wave peak detection method according to an embodiment of the present invention.
Figure 4:
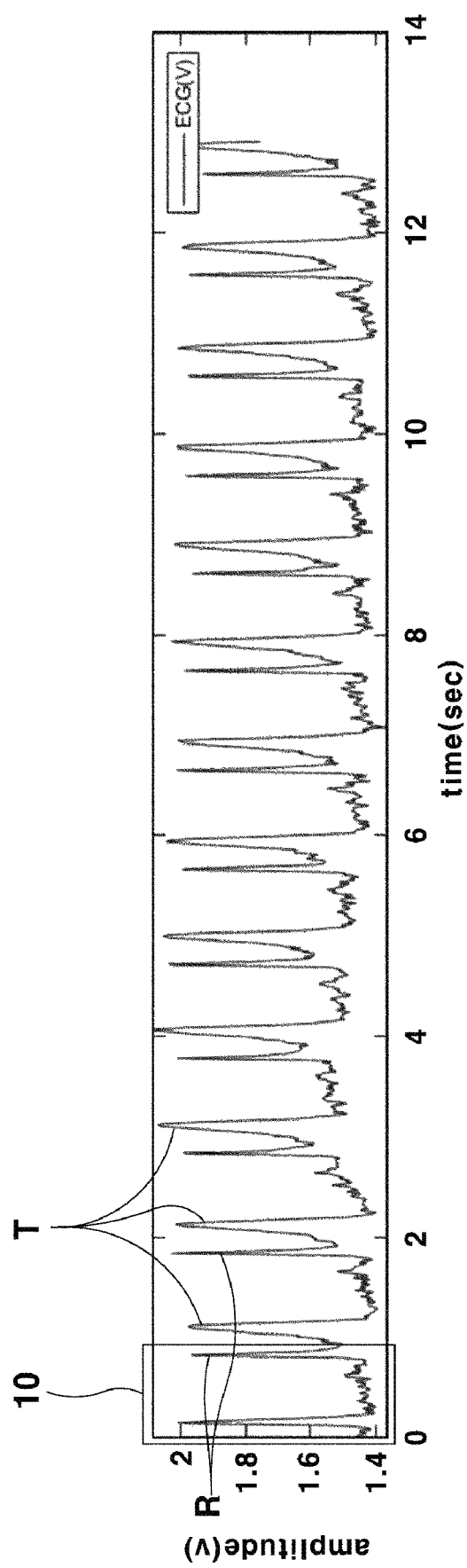
FIG. 4 is a diagram illustrating an initial region setting of an electrocardiogram signal in an R wave peak detection method according to an embodiment of the present invention.
Figure 5:
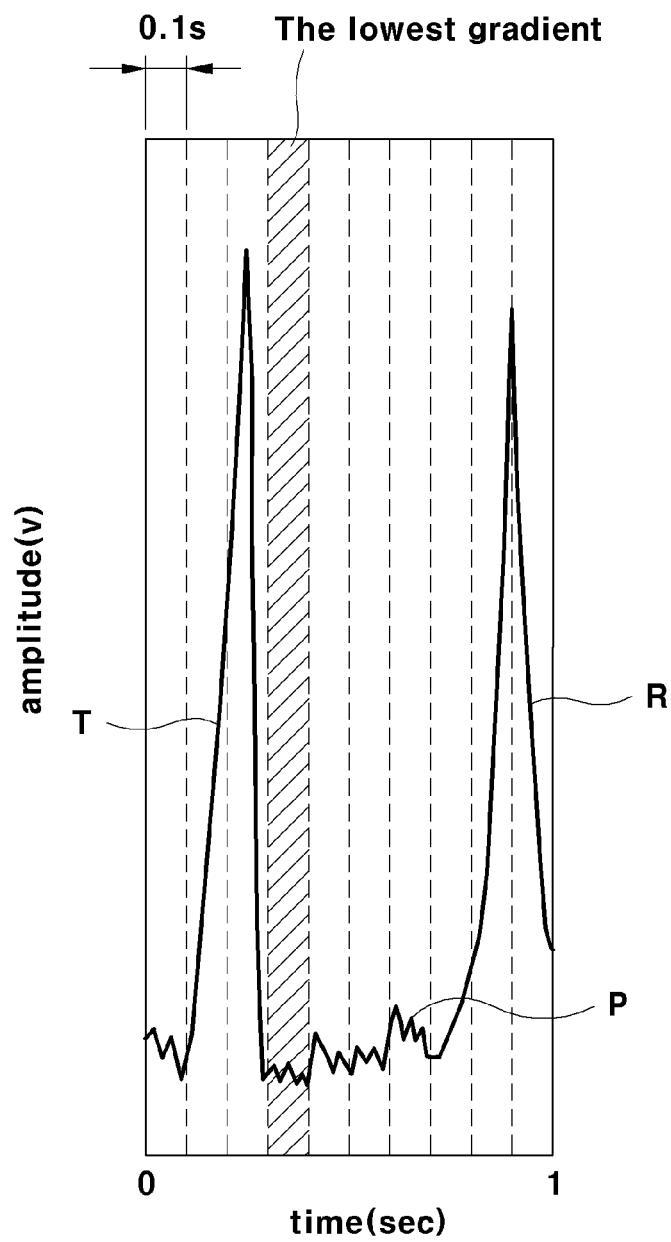
FIG. 5 is a diagram illustrating a section having the lowest gradient in the initial region in an R wave peak detection method according to an embodiment of the present invention.
Figure 6:
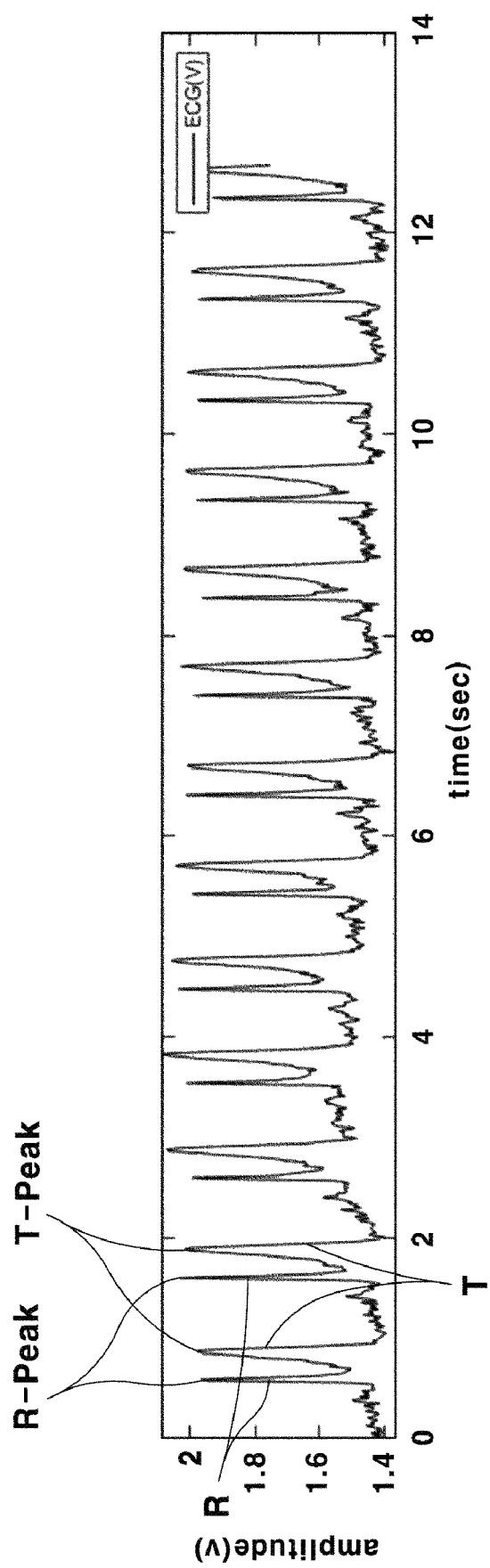
FIG. 6 is a diagram illustrating an electrocardiogram signal in which an electrocardiogram signal preceding a section having the lowest gradient is removed in an R wave peak detection method according to an embodiment of the present invention.

FIG. 3 is a flowchart illustrating a method of removing a signal preceding a section having the lowest gradient from an electrocardiogram signal in an R wave peak detection method according to an embodiment of the present invention, FIG. 4 is a diagram illustrating an initial region setting of an electrocardiogram signal in an R wave peak detection method according to an embodiment of the present invention, FIG. 5 is a diagram illustrating a section having the lowest gradient in the initial region in an R wave peak detection method according to an embodiment of the present invention, and FIG. 6 is a diagram illustrating an electrocardiogram signal in which an electrocardiogram signal preceding a section having the lowest gradient is removed in an R wave peak detection method according to an embodiment of the present invention.

Referring to FIGS. 3 to 6, a step S200 of removing the signal preceding a section having the lowest gradient from the electrocardiogram signal is performed by setting an initial region 10 in the electrocardiogram signal (S2100).

Meanwhile, the electrocardiogram signal having similar characteristics of R waveform (R) and T waveform (T) is used in order to verify the R wave detection method according to the present invention.

In addition, the initial region 10 is used to obtain a gradient of only a predetermined region in the electrocardiogram signal, and the sampling range for obtaining the gradient of the electrocardiogram signal is zero to one second.

Next, sections are set by dividing a range of the set initial region 10 by a predetermined time (S2200).

In addition, the setting of the sections is performed by dividing the initial region 10 into a total of 10 sections on a per-0.1 second basis, and the number of data of the electrocardiogram signal included every 0.1 seconds may be varied depending on the sampling rate.

Next, the gradient is calculated using the data of the electrocardiogram signal corresponding to the divided section (S2300).

In addition, the gradient is the amount of change in the electrocardiogram signal over time. When the number of data of the electrocardiogram signal corresponding to one section is 13, the gradient between the current electrocardiogram signal data and the next electrocardiogram signal data is sequentially calculated, and herein a total of 12 gradients are derived.

Also, the derived 12 gradients are converted to absolute values, the final gradient of the corresponding section is defined by obtaining an average of the 12 gradients converted to absolute values.

Next, a section having the lowest gradient of gradients calculated for each section is detected, and the sections preceding the detected section are removed from the electrocardiogram signal (S2400).

Meanwhile, a section having the lowest gradient indicates that data values of the electrocardiogram signal indicates the same with almost no variation. Generally, the section appears between a P waveform (P) and a T waveform (T) preceding the P waveform (P) in the electrocardiogram signal and has the lowest gradient.

Therefore, preprocessing is performed for a waveform at the point of time when the electrocardiogram signal starts so that the P waveform, the QRS complex, and the T waveform sequentially appear.

Next, an expected R wave peak from the electrocardiogram signal is detected (S3000).

In addition, a Pan-Tompkins algorithm is used to detect the expected R wave peak in the present invention, but various other algorithms may be used to detect the expected R wave peaks.

Figure 7:
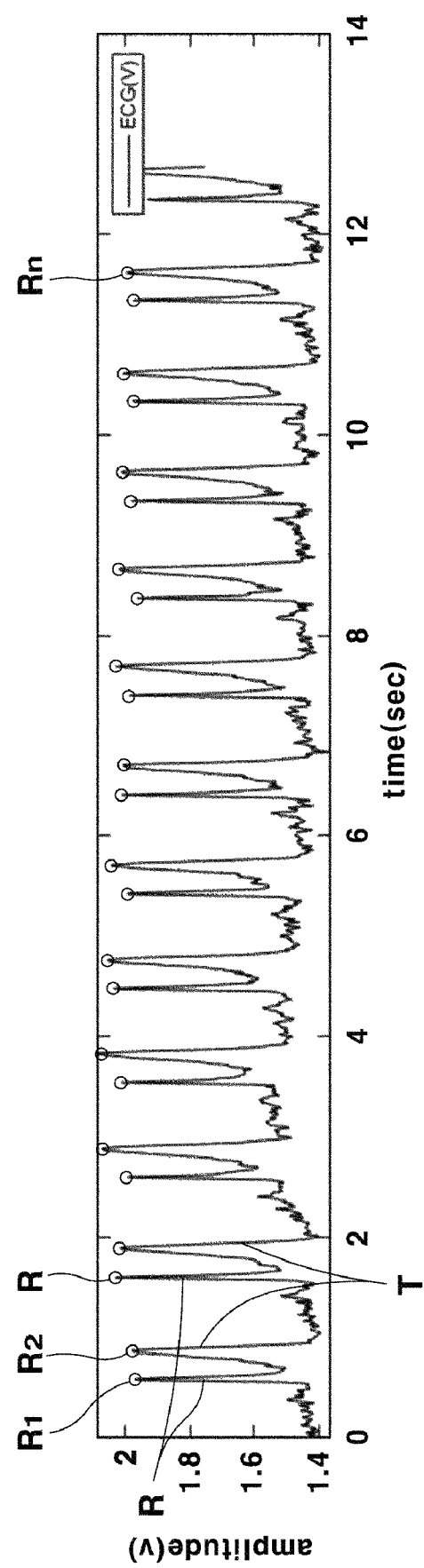
FIG. 7 is a diagram illustrating an electrocardiogram signal in which an expected R wave peak is detected in an R-wave peak detection method according to an embodiment of the present invention.

FIG. 7 is a diagram illustrating an electrocardiogram signal in which an expected R wave peak is detected in an R-wave peak detection method according to an embodiment of the present invention.

Also, in the expected R wave peaks ($R_1$, $R_2$, $R_3$, . . . , and $R_n$) detected through the Pan-Tompkins algorithm, it may be appreciated that not only the actual R wave peak (R-peak), but also the actual T wave peak (T-Peak) are detected as the expected R wave peaks ($R_1$, $R_2$, $R_3$, . . . , and $R_n$).

Next, the actual R wave peak is detected by substituting the times at which the expected R wave peaks ($R_1$, $R_2$, $R_3$, . . . , and $R_n$) are detected into Equation 1 below (S4000).

$$\text{if } |R_n - R_{n+1}| \le Th \begin{cases} 0, & R_{n+1} \\ 1, & \text{None} \end{cases} \quad \text{[Equation 1]}$$

$$n = 1, 2, 3, 4, \ldots$$

Wherein, $R_n$ is the time at which the nth expected R wave peak is detected, and Th is a threshold time difference.

In addition, it is preferable that the threshold time difference is set to 0.4. That is because a time difference between the Q waveform and the R wave peak detected in a general electrocardiogram signal is 0.05 seconds and a time difference between the Q waveform and the T waveform is equal to or less than 0.45 seconds, whereby the R wave peak may not exist below the threshold time difference, and the threshold time difference is set based thereon.

According to Equation 1, when an absolute value of the subtraction of $R_n$ and $R_{n+1}$ is equal to or less than the threshold time difference, $R_{n+1}$ is extracted, and otherwise no data is output.

Figure 8:
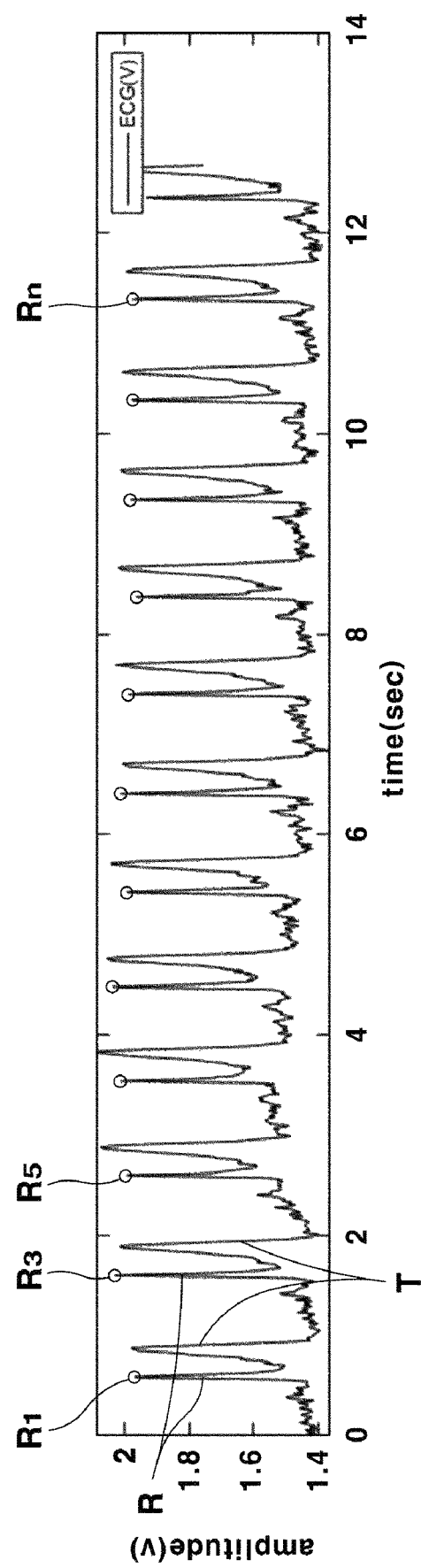
FIG. 8 is a diagram illustrating an electrocardiogram signal in which an expected R-wave peak erroneously detected is removed in an R wave peak detection method according to an embodiment of the present invention.

FIG. 8 is a diagram illustrating an electrocardiogram signal in which an expected R-wave peak erroneously detected is removed in an R wave peak detection method according to an embodiment of the present invention. Referring to FIG. 8, $R_{n+1}$ extracted according to the condition of Equation 1 is excluded from the expected R wave peaks ($R_1$, $R_2$, $R_3$, . . . , and $R_n$), and the remaining expected R wave peaks ($R_1$, $R_2$, $R_3$, . . . , and $R_n$) are output.

That is, the $R_{n+1}$ extracted according to the condition of Equation 1 is an erroneously detected R wave peak, and is thus removed from the expected R wave peaks ($R_1$, $R_2$, $R_3$, . . . , and $R_n$) and the remaining expected R wave peaks ($R_1$, $R_2$, $R_3$, . . . , and $R_n$) are output as actual R wave peaks.

In addition, since the point of time at which the electrocardiogram signal starts is started from the P waveform (P) through the step (S2000) of removing the signal preceding the section having the lowest gradient from the electrocardiogram signal, the initial expected R wave peak $R_1$ is defined as the actual R wave peak (R-Peak).

Therefore, the R wave peak detection method using the periodicity of the electrocardiogram signal according to the present invention may be provided to remove the expected R wave peaks in which a time difference between the expected R wave peaks that are detected is equal to or less than the threshold time difference, whereby the actual R wave peak can be detected through a simple equation without a complex algorithm and the accuracy of R wave peak detection can be improved.

While the present invention has been particularly shown and described with reference to exemplary embodiments thereof, the present invention is not limited to the above-mentioned embodiments, and it will be understood by those skilled in the art that various changes in form and details may be made therein without departing from the spirit and scope of the invention as defined by the appended claims.

What is claimed is:

1. An R wave peak detection method using a periodicity of an electrocardiogram signal, the method comprising:
    receiving the electrocardiogram signal;
    removing signals preceding a section having a lowest gradient from the electrocardiogram signal by a process comprising:
        setting an initial region to sample amplitude values in the electrocardiogram signal;
        setting sections by dividing the set initial region by a predetermined time;
        sampling the amplitude values corresponding to each of the divided sections and calculating the gradient that is a variation of the amplitude values with time; and
        extracting the section having the lowest gradient and removing signals preceding the extracted section from the electrocardiogram signal,
    wherein when the expected R wave peaks are detected in the electrocardiogram signal, an initial expected R wave peak is defined as the actual R wave;
    detecting expected R wave peaks of the electrocardiogram signal; and
    detecting and removing the expected R wave peaks in which a time difference between the expected R wave peaks is equal to or less than a threshold time difference and extracting remaining expected R wave peaks as actual R wave peaks, the detecting and removing of the expected R wave peaks performed by Equation 1:

$$\text{if } |R_n - R_{n+1}| \leq Th \begin{cases} 0, & R_{n+1} \\ 1, & \text{None} \end{cases} \quad \text{[Equation 1]}$$

wherein n=a natural number;
$R_n$ is a time at which the $n^{th}$ expected R wave peak is detected; and
Th is a threshold time difference; and
when the time difference between $R_n$ and $R_{n+1}$ is equal to or less than the threshold time difference, the expected R wave peak corresponding to $R_{n+1}$ is removed.

2. The method of claim 1, wherein the expected R wave peaks of the electrocardiogram signal are detected using a Pan-Tompkins algorithm.

3. A computer program stored on a recording medium for performing the method of claim 2.

4. The method of claim 1, wherein the threshold time difference is 0.4 seconds.

5. A computer program stored on a recording medium for performing the method of claim 4.

6. A computer program stored on a recording medium for performing the method of claim 1.

7. A computer program stored on a recording medium for performing the method of claim 1.

* * * * *